United States Patent
Lundquist et al.

(10) Patent No.: US 7,805,081 B2
(45) Date of Patent: Sep. 28, 2010

(54) METHODS AND SYSTEMS FOR MONITORING MULTIPLE OPTICAL SIGNALS FROM A SINGLE SOURCE

(75) Inventors: Paul Lundquist, San Jose, CA (US); Stephen Turner, Menlo Park, CA (US); Denis Zaccarin, San Jose, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 362 days.

(21) Appl. No.: 11/201,768

(22) Filed: Aug. 11, 2005

(65) Prior Publication Data

US 2007/0036511 A1     Feb. 15, 2007

(51) Int. Cl.
*H04B 10/00* (2006.01)

(52) U.S. Cl. .......................... 398/140; 398/109; 398/9; 398/25

(58) Field of Classification Search ......... 398/202–214, 398/118–131
See application file for complete search history.

(56) References Cited

U.S. PATENT DOCUMENTS

| | | | | |
|---|---|---|---|---|
| 5,239,178 A | * | 8/1993 | Derndinger et al. | 250/234 |
| 5,470,710 A | * | 11/1995 | Weiss et al. | 435/6 |
| 5,491,344 A | * | 2/1996 | Kenny et al. | 250/461.1 |
| 5,545,531 A | * | 8/1996 | Rava et al. | 506/23 |
| 5,547,839 A | | 8/1996 | Dower et al. | |
| 5,578,832 A | * | 11/1996 | Trulson et al. | 506/39 |
| 5,631,734 A | * | 5/1997 | Stern et al. | 356/317 |
| 5,677,196 A | * | 10/1997 | Herron et al. | 436/518 |
| 5,695,934 A | * | 12/1997 | Brenner | 435/6 |
| 5,744,305 A | * | 4/1998 | Fodor et al. | 506/16 |
| 5,821,058 A | | 10/1998 | Smith et al. | |
| 5,828,452 A | * | 10/1998 | Gillispie et al. | 356/328 |
| 6,071,748 A | * | 6/2000 | Modlin et al. | 436/174 |
| 6,210,896 B1 | * | 4/2001 | Chan | 435/6 |
| 6,236,945 B1 | * | 5/2001 | Simpson et al. | 702/20 |
| 6,263,286 B1 | * | 7/2001 | Gilmanshin et al. | 702/19 |
| 6,271,039 B1 | * | 8/2001 | Palmer et al. | 436/166 |
| 6,388,788 B1 | * | 5/2002 | Harris et al. | 359/196 |
| 6,571,118 B1 | * | 5/2003 | Utzinger et al. | 600/476 |
| 6,603,537 B1 | * | 8/2003 | Dietz et al. | 356/39 |
| 6,690,002 B2 | | 2/2004 | Kuroda et al. | |
| 6,699,655 B2 | * | 3/2004 | Nikiforov | 435/4 |
| 6,784,982 B1 | * | 8/2004 | Blumenfeld et al. | 356/71 |

(Continued)

FOREIGN PATENT DOCUMENTS

EP     1105529 B1     9/2005

(Continued)

OTHER PUBLICATIONS

M. J. Levene, et al., "Zero-Mode Waveguides for Single-Molecule Analysis at High Concentrations," *Science*, 299:682-686 (Jan. 31, 2003).

*Primary Examiner*—Agustin Bello
(74) *Attorney, Agent, or Firm*—Robert H. Reamey; Matthew B. Murphy

(57) ABSTRACT

Methods and systems for monitoring a plurality of different optical signals from a single source of such signals, where each such different optical signal is spatially separated from other such signals and directed to different detectors or locations upon a single detector, which direction is generally accomplished through the use of a small number of optical components and/or manipulations.

40 Claims, 5 Drawing Sheets

U.S. PATENT DOCUMENTS

| | | | |
|---|---|---|---|
| 6,800,860 B2* | 10/2004 | Dietz et al. | 250/458.1 |
| 6,818,395 B1 | 11/2004 | Quake et al. | |
| 6,867,851 B2* | 3/2005 | Blumenfeld et al. | 356/73 |
| 6,869,764 B2 | 3/2005 | Williams et al. | |
| 6,917,726 B2 | 7/2005 | Levene et al. | |
| 6,919,211 B1* | 7/2005 | Fodor et al. | 506/18 |
| 6,979,830 B2* | 12/2005 | Dietz et al. | 250/485.1 |
| 6,982,146 B1 | 1/2006 | Schneider et al. | |
| 7,008,766 B1* | 3/2006 | Densham | 435/6 |
| 7,033,762 B2 | 4/2006 | Nelson et al. | |
| 7,033,764 B2 | 4/2006 | Korlach et al. | |
| 7,052,847 B2 | 5/2006 | Korlach et al. | |
| 7,056,661 B2 | 6/2006 | Korlach et al. | |
| 7,056,676 B2 | 6/2006 | Korlach et al. | |
| 7,064,197 B1 | 6/2006 | Rabbani et al. | |
| 7,081,954 B2* | 7/2006 | Sandstrom | 356/317 |
| 7,083,914 B2* | 8/2006 | Seul et al. | 435/6 |
| 7,130,041 B2 | 10/2006 | Bouzid et al. | |
| 7,135,667 B2* | 11/2006 | Oldham et al. | 250/208.1 |
| 7,139,074 B2 | 11/2006 | Reel | |
| 7,145,645 B2* | 12/2006 | Blumenfeld et al. | 356/73 |
| 7,180,589 B2* | 2/2007 | Couston et al. | 356/318 |
| 7,189,361 B2 | 3/2007 | Carson | |
| 7,199,357 B1 | 4/2007 | Oldham et al. | |
| 7,209,836 B1* | 4/2007 | Schermer et al. | 702/19 |
| 7,227,128 B2 | 6/2007 | Sagatelyan | |
| 7,233,393 B2 | 6/2007 | Tomaney et al. | |
| 7,292,742 B2* | 11/2007 | Levene et al. | 385/12 |
| 7,302,348 B2* | 11/2007 | Ghosh et al. | 702/19 |
| 7,323,681 B1 | 1/2008 | Oldham et al. | |
| 2003/0044781 A1* | 3/2003 | Korlach et al. | 435/6 |
| 2003/0077610 A1 | 4/2003 | Nelson et al. | |
| 2003/0174324 A1 | 9/2003 | Sandstrom | |
| 2003/0174992 A1 | 9/2003 | Levene et al. | |
| 2003/0186276 A1 | 10/2003 | Odera | |
| 2003/0190647 A1 | 10/2003 | Odera | |
| 2003/0194740 A1 | 10/2003 | Williams | |
| 2003/0215862 A1 | 11/2003 | Parce et al. | |
| 2004/0048301 A1 | 3/2004 | Sood et al. | |
| 2004/0130716 A1* | 7/2004 | Couston et al. | 356/318 |
| 2004/0224319 A1 | 11/2004 | Sood et al. | |
| 2005/0064427 A1* | 3/2005 | Gluch et al. | 435/6 |
| 2005/0135974 A1 | 6/2005 | Harvey et al. | |
| 2005/0206895 A1 | 9/2005 | Salmelainen | |
| 2007/0048748 A1* | 3/2007 | Williams et al. | 435/6 |
| 2007/0099212 A1* | 5/2007 | Harris | 435/6 |
| 2007/0196815 A1* | 8/2007 | Lappe et al. | 435/4 |
| 2008/0020938 A1 | 1/2008 | Kaplan | |

FOREIGN PATENT DOCUMENTS

| | | |
|---|---|---|
| WO | WO 91/06678 | 5/1991 |
| WO | WO 96/27025 | 9/1996 |
| WO | WO 99/05315 | 2/1999 |
| WO | WO 00/36152 | 6/2000 |
| WO | WO 01/16375 A2 | 3/2001 |
| WO | WO 2004/100068 A2 | 11/2004 |
| WO | WO 2006/116726 A2 | 2/2006 |
| WO | WO 2006/135782 A2 | 12/2006 |
| WO | WO 2007/002367 A2 | 1/2007 |
| WO | WO 2007/011549 A1 | 1/2007 |
| WO | WO 2008/002765 A2 | 1/2008 |

\* cited by examiner

METHODS AND SYSTEMS FOR MONITORING MULTIPLE OPTICAL SIGNALS FROM A SINGLE SOURCE

CROSS-REFERENCE TO RELATED APPLICATIONS

Not Applicable.

STATEMENT REGARDING FEDERALLY SPONSORED RESEARCH

Not Applicable.

BACKGROUND OF THE INVENTION

The individual identification, distinction and/or quantitation of different optical signals from a collection of such signals is of major importance in a number of different fields. Of particular note is the use of multiplexed analytical operations, e.g., chemical assays, etc., which employ optical signaling events that have different optical characteristics which may then be identified and potentially quantified separately from each other optical signal. Such analytical assays include medical diagnostic tests, food and other industrial process analyses, and basic tools of biological research and development. While a wide variety of optical and chemical approaches have been applied toward analysis of these signals, such systems often include a level of complexity and/or cost that detracts from the overall utility of the approach, particularly for operations that require high levels of sensitivity. The present invention addresses these shortcomings of other systems and methods.

BRIEF SUMMARY OF THE INVENTION

The present invention generally provides methods and systems for detecting and monitoring a plurality of different optical signals from a single, preferably confined source of such signals. In preferred aspects, such systems and methods are applied to the detection of luminescent or fluorescent signals from fluid borne materials and particularly reactants and/or products of chemical, biochemical or biological reactions of interest.

In a first aspect, the present invention provides methods of detecting optical signals, where such methods comprise providing a source of at least first and second optical signals wherein the first optical signal comprises an optical characteristic different from an optical characteristic of the at least second optical signal. In preferred aspects, the optical characteristic is a wavelength of the optical signals. The optical signals are directed to different locations on a detector, e.g., by passing the signals through an optical train that transmits the first and second optical signals in divergent paths, and then received at different locations on one optical detector.

In a related aspect, the method of detecting optical signals, comprises providing a source of a plurality of different optical signals, wherein each different optical signal comprises a wavelength different from each other optical signal, and spatially separating the plurality of different optical signals and directing them to discrete locations on one optical detector.

In a further aspect, a method is provided for detecting optical signals, which method comprises providing a confined source of at least first and second optical signals wherein the first optical signal comprises a different optical characteristic, i.e., wavelength, from that of the at least second optical signal. The signals are then spatially separated and directed to first and second different locations on a first optical detector.

The present invention also provides for systems useful in carrying out the foregoing methods. For example in one aspect, the invention provides analytical systems, comprising a confined reaction region for containing a reaction mixture that produces at least first and second optical signals wherein the first optical signal comprises an optical characteristic different from that of the at least second optical signal. Such systems also comprise an optical train in optical communication with the confined reaction region, for receiving the first and second optical signals and spatially separating the first and second optical signals and directing them to different locations on an optical detector.

Related systems of the invention comprise a confined reaction region for containing a reaction mixture that produces at least first and second optical signals wherein the first optical signal comprises a wavelength different from a wavelength of the at least second optical signal, an optical train in optical communication with the confined reaction region, for receiving the first and second optical signals and spatially separating the first and second optical signals and directing them to different locations on an optical detector. In alternate aspects, the optical train comprises a replaceable modular optical component that spatially separates the first and second optical signals passing therethrough. By selecting different modules from a collection or library of modules, one can increase the usefulness of the overall system.

DETAILED DESCRIPTION OF THE INVENTION

I. General

Figure 1B:
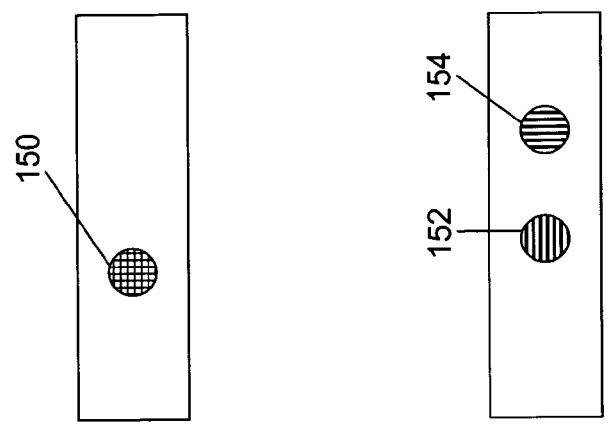
FIG. 1 provides a simplified schematic illustration of the methods and system of the invention.

The present invention is generally directed to devices, systems and methods for the facile, efficient and cost effective analysis and/or management of collections of optical signals and the data derived from those signals. Of particular interest is the application of these devices, systems and methods in analyzing reactions of interest, e.g., chemical and biochemical reactions such as nucleic acid synthesis, and the characterization of the steps involved in those reactions.

In general, the present invention is directed to methods, systems and devices for measuring two or more different optical signals from a source of optical signals, by separating the optical signals from each other and directing them to different detection functionalities, or different locations, on a single optical detector. By separately detecting the different optical signals one can recognize the occurrence of the causal events for each signal. In addition, by doing so within few detectors or a single detector or detector array, one can reduce the complexity and cost of systems and their associated control and analysis processes, while concurrently increasing their efficiency and/or sensitivity.

While the overall systems and methods of the invention may be employed broadly in a wide range of different applications, of particular interest is the use of these systems and methods in the analysis and characterization of chemical and/or biochemical reactions, which either naturally or artificially produce such differing optical signals during the reaction process. There are a wide variety of different analytical reactions that produce multiple optical signals that would benefit from the present invention. These include reactions that use optical signals of differing wavelengths, e.g., fluorescent and/or fluorogenic reactants or products, luminescent reactants or products, chromophoric and/or chromogenic reactants or products, etc., and reactions that use optical signals that differ in other characteristics, e.g., shifts in polarization or phase modulation of emitted light. In general, as used herein, reference to a wavelength of an optical signal includes a wavelength range for that signal. In particular, optical signals, e.g., emitted fluorescence, luminescence, or the like, will span a portion of the optical spectrum which portion may span a range of from 1 nm to 30 nm up to 100 nm or more within the overall spectrum. In terms of the present invention, optical signals of different wavelengths denote signals whose wavelength range is distinguishable from the other. Thus while little or no overlap of the wavelength ranges for different signals would be ideal, a substantial amount of wavelength overlap may be tolerated, provided that signals may be individually identified. Methods of identification and distinction of signals from signal overlap or noise in optical systems, i.e., through the use of optical components and/or through stringent data selection, is well known in the art. In a particularly preferred aspect, the analytical methods and systems of the invention are applied in nucleic acid analyses and particularly nucleic acid sequence analyses.

Because the methods and systems of the invention have reduced complexity, and as a result, higher sensitivity, they are particularly useful in applications where the optical signals to be detected are relatively weak, e.g., low light levels, few signal events, etc. In particular, because the systems employed in the invention minimize the number of optical manipulations that signals are put through, the overall efficiency losses of the system that are summed from each such manipulation are likewise reduced. For example, where optical signals are passed through multiple beam splitting, refocusing, filtering, etc. operations, losses associated with each stage can dramatically reduce the sensitivity of the overall assay. Additionally, losses associated with examining only a separate portion of the optical spectrum of the overall signal, e.g., using restrictive band-pass filters and the like, can further reduce the amount of signal that could otherwise be used in the detection operation. In the case of the methods and systems of the invention, the entire spectrum of the overall signal is subjected to detection, and selection of each different signal component is a matter of selecting the location on a single detector, e.g., which pixels in a detector array, should be applied toward assessing a given signal, rather than cutting off a portion of signal before it is ever detected through, e.g., optical cut-off filtering.

While many applications begin with more than adequate signal strength to allow for such losses, some applications operate at signal levels that, when combined with the efficiency losses, are either below the level of meaningful detection of the overall system, or the effect of interest is a change to the optical signal where such change is within the noise level of the system, e.g., the signal is so small as to be indistinguishable from random fluctuations in signal intensity. Examples of these low signal types of applications include, for example, low concentration chemical analyses such as single or few molecule reactions, and the like, where very few or even a single detectable molecule may be all that is available to be detected at any given time.

II. Methods

As noted above, in one aspect, the invention is directed to methods of detecting optical signals, from a source of a plurality of different optical signals, by separating the different optical signals from each other and directing at least a portion of them to discrete locations on one optical detector or detector array. In the case where multiple signals are detected at different locations on a single detector, it will be understood that such detector includes or is capable of being configured to provide signal information for signals incident thereon, that correlate not only the signal intensity and time, but also the position or location upon the array at which such signal is incident. Simple examples of such detectors include array type detectors as are generally known in the optics art, and certain examples of which are described in greater detail herein. In the case where single point signals are to be detected at discrete detectors, it will be understood that position information of an incident signal is provided by the location of each individual detector (typically although not necessarily of a plurality of individual detectors), rather than a location within one single detector or detector array.

While the methods of the invention could be applied to a wide variety of types of sources of optical signals, in preferred aspects, the source of optical signals comprises a confined source. The confined sources of the inventions are typically characterized in that one or more components of the source that produce the particular optical signals are confined in space, and are not flowing into and or out of the confined source during the detection. Such confined sources are in contrast to systems where signal producing components, reactants, or the like are actively flowing past a point of detection in a conduit. Notwithstanding the foregoing, components of the signal producing mechanism employed in the invention may be diffusing into and out of the confined space, while still falling within the parameters set forth herein. In many cases, however, one or more components that contribute to the signaling mechanism will be immobilized within the confined space.

The confined nature of the sources is of particular value where the optical signals result from reactive chemical species and particularly fluid borne reactive chemical species, e.g., aqueous and/or organic fluids. In particular, in the case of fluid sources of differing optical signals, the confined nature of the source would not permit the movement of such fluids into or out of the confinement during detection. Examples of fluid confinements include, e.g., conventional multiwell analysis plates, e.g., 96, 384 or 1536 well plates. Other examples of confinements for such fluid reactants include nanoscale wells or apertures, i.e., zero mode waveguide structures as described in Published U.S. patent application Ser. No. 2003/0174992 A1, which is incorporated herein by reference in its entirety for all purposes, which serve as both physical confinements and optical confinements, e.g., limiting the amount of light that penetrates into the waveguide and thus effectively limiting the volume from which signals, e.g., fluorescent signals, emanate. Such zero mode waveguides are particularly useful in the exploitation of the invention, in that they provide the ability to monitor different optical signals from vary small volumes, e.g., fluid borne reactants, allowing monitoring of interactions between few molecules, etc. Thus, while a zero-mode waveguide may represent the confined space, the observed volume of that confined space is a fraction of the volume of such space, as is determined in part by the dimensions of the waveguide. This fractional observed volume represents a further confinement of the signal source. Of particular interest is the use of such confined volumes in single molecule interactions, such as DNA sequence identification through the stepwise reaction of labeled nucleotide analogs with a nucleic acid polymerase in template dependent nucleic acid synthesis, molecular interaction monitoring, i.e., DNA hybridization, immunoassays, enzymatic reactions, and the like.

In addition to structural confinement, e.g., using wells, reservoirs or the like, confinement may additionally or alternatively comprise chemical immobilization of chemical species that produce one or more of the optical signals, i.e., either in place of or in addition to any structural confinement. Examples of such chemical confinement include covalent, van der waals or other associative interactions between chemical species and substrate surfaces, use of chemical interactions to create structural confinements, e.g., substrates having hydrophilic regions surrounded by hydrophobic barriers to confine fluid and chemical species, and the like. In the case where confinement denotes chemical immobilization of reactants in a given location, a variety of different immobilization techniques may be employed, including, e.g., covalent linkage of reactants onto surfaces of supports or substrates, including for example silane or epoxide linkages. Likewise, other associative linkages may be employed using, e.g., complementary binding pairs to couple reactants to substrates or supports. Such linkages include, e.g., antibody/antigen linkages, biotin/avidin linkages, and the like. In the case of chemically created structural confinements, again, a variety of techniques are available for providing such 'structures' on substrates. In particular, hydrophobic barriers may be created by providing alkylsilane groups on otherwise hydrophilic silica surfaces. Such materials are readily patterned onto substrate surfaces using conventional photolithographic techniques, screen printing, ink-jet printing or the like, to define hydrophilic confines surrounded by hydrophobic barrier regions.

As alluded to above, in preferred aspects the optical signals emanating from the source derive from reactive chemical species, where the reaction of such species either produces, extinguishes, increases, decreases, or otherwise alters the characteristic of the optical signals. Such reactive species include chromogenic or chromophoric reactants, e.g., that produce a shift in the transmissivity of the material to light of one or more wavelengths, i.e., changing color upon reaction. Reactant species that emit light, either with the use of an activating light source (fluorescent or fluorogenic) or without such an excitation source (luminescent) are preferred for use in the methods of the invention. Further, in the context of the invention, such reactive species are most preferably contained in fluid solutions and are provided as reaction mixtures where the different optical signals result from the substrates, the products, or combinations of the two.

In preferred aspects, as noted above, the different optical signals to be detected are comprised of light of differing wavelengths, e.g., emitted by different fluorophores where such emissions have different wavelength spectra, or transmitted by different chromophores where such transmissions are at different wavelength spectra. In such cases, the two or more different optical signals are spatially separated, e.g., through the use of a beam splitter in combination with one or more dichroic filters, or through the use of a prism or optical grating, and the different signals are directed to different locations on an optical detector or detector array. In alternate aspects, the different optical signals may differ in other characteristics, such as their relative polarity, their modulation phase or frequency, or the like, provided that they may be spatially separated and directed to different regions on a detector or detector array, e.g., through the use of polarizing or demodulation filters. Examples of biochemical assays based upon such differing characteristics are described in, e.g., U.S. Pat. No. 6,699,655, which discloses monitoring reaction progress by detecting of the relative polarity of fluorescent reactants and products (typically in combination with a polarization affecting agent) when excited with polarized light.

The methods of spatial separation and/or direction of different optical signals to different locations on an optical detector or detector array is generally dependent upon the characteristic(s) of the different optical signals that is/are to be the basis of differential detection. For example, where the different optical signals differ in their wavelength, separation and direction can be accomplished through the use of optical filters and/or prisms that selectively transmit or redirect light of differing wavelengths in different manners and/or to different degrees. For example, a collected signal that comprises two different wavelengths of light emanating from a confined source may be split into two beams, e.g., through the use of a dichroic filter to remove the other signal component, then passed through a barrier filter, thereby allowing only a portion of the overall signal to be directed to the optical detector or detector array. In accordance with the invention, however, a simpler optical train is employed to separate optical signals and direct them to different locations on a detector or detector array, or in some cases, to multiple different detectors or detector arrays. In particular, a wedge prism or optical grating may be employed to achieve this result. The use of such prisms or diffraction gratings provides simplicity to the optical train of the overall system and results in a more transmissive light path as compared to more complex optical systems. Additionally, in contrast to the use of cut-off filters, e.g., dichroics, the entire spectrum of signal, or at least a more selectively filtered portion of the signal, less, e.g., the reflective losses of the prism, may be directed to the detector or detector array. As a result, there is a greater amount of signal available for detection, manipulation and deconvolution. The simplicity of the invention provides further advantages in the flexibility of the system, where a single instrument may be easily configured to perform a wide range of different operations, e.g., perform operations that each employ different ranges of optical signals, by simply replacing an interchangeable prism portion of the optical train with another prism from a library or collection of different prisms. Reconfiguration of conventional multifilter optical trains, by contrast, would require much more substantial alteration, e.g., changing multiple filters, etc. In particular, in accordance with certain aspects of the invention, the component of the optical train that spatially separates the optical signals may comprise a modular, and easily replaceable component, such as a prism, multiple prisms, and/or optical grating(s), that can be inserted into and ejected from an appropriate receiver slot on an instrument. Further, a given instrument may be supplied with ort suppliable with a library of such modular components, where each of the components provides different optical dispersion profiles for different optical signals or collections of optical signals, allowing facile reconfiguration of the separation component by the end user and maximal usefulness and flexibility to the user. Some exemplary optical trains are described in greater detail herein.

In keeping with the simplicity of the optical trains described herein, the ultimate detection of multiple optical signals in parallel is typically accomplished through the use of smaller numbers of detectors. In particular, detection of n optical signals (where n>1) is typically accomplished through the use of at most, n−1 discrete detectors. In particularly preferred aspects, as many as 2, 3, 4, 5, 6 or more different optical signals are directed to different locations on 1, or in cases of 3 or more signals, 2 or more discrete optical detectors or detector arrays. In accordance with the invention, it will be appreciated that in cases where more than one signal is directed to more than one location on a given detector, such detectors are not single point detectors, e.g., simple photodiodes, but instead have a detection area that generates a signal that is indicative of the incidence of an optical signal on the detector, as well as an indication of the location on the detector where such signal was incident. Examples of such detectors include imaging detectors, such as charge coupled devices (CCDs), where each pixel element on the CCD constitutes a single point detector, but the overall device constitutes an array of detectors, where the detector signal indicates the pixel at which the signal was incident and the intensity of that signal at that pixel. Similarly, larger diode array detectors may be used that include larger numbers of photodiodes spatially arranged and interfaced to provide both signal intensity and signal location information within the array. Notwithstanding the foregoing, simple point detectors may be used in conjunction with such detector arrays in accordance with the invention, e.g., where single signals are directed to a single detector, and different signals are directed to different, or discrete detectors, rather than to regions on the same detector.

Although primarily and preferably directed at methods and systems where multiple optical signals are directed at one detector or detector array, or detectors that number less than the number of different optical signals to be detected, in certain alternative aspects, where optical signals that differ in wavelength are spatially separated using, e.g., an optical grating or color dispersive prism, e.g., a wedge prism, each different signal is optionally directed to a different detector element, e.g., a point detector. In such cases, the incorporation of simple and cost effective separation optics, e.g., a prism or optical grating, provides enhanced efficiency over more complex optical trains, both in terms of financial costs and in terms of optical efficiency. Thus, while the simplicity of using a single detector or detector array is not found, efficiencies of costs may still exist where multiple lower cost point detectors or lower resolution detector arrays are employed as the detector elements. Further, such systems still retain the substantial efficiencies of cost over more complex systems and methods.

Based upon the spatial separation and direction, the incidence of an optical signal at a particular location on the detector or detector array indicates that one of the two optical signals is being emitted or transmitted from the confined source. If two or more locations on the detector or elements on the detector array indicate the incidence of an optical signal, it is indicative that two or more different optical signals are being emitted. By monitoring the particular location or element that is indicating an incident signal, one can identify which signal is being emitted, and based upon the reaction being carried out, identify the reaction condition that is occurring, e.g., the generation of a given product or consumption of a given reactant.

Figure 1A:
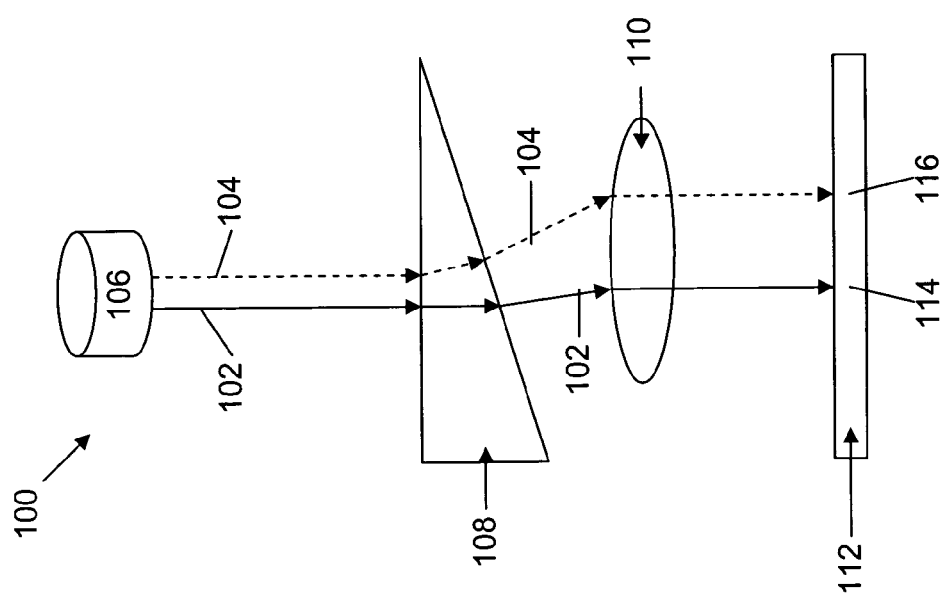

A simplified schematic of the methods of the invention is illustrated in FIG. 1A. As shown, in a system 100, at least two different optical signals 102 and 104 emanate from a confined source 106 of such signals. As noted elsewhere herein, such confined sources may preferably be defined locations that comprise fluid borne chemical reactants, such as reaction wells or regions, zero mode waveguides, etc. The different optical signals are then spatially separated (as shown by the divergent paths of solid arrows 102 and dashed arrows 104) by passing those signals through an appropriate optical component, e.g., prism 108, an optical grating or the like. Once separated, the signals are focused through lens 110, e.g., an imaging lens, causing them to impinge on detector array 112 at two different locations 114 and 116 on that detector array 112. The separation of signals is illustrated schematically in FIG. 1B. In particular, the combined optical signals enter prism 108 as a signal as represented by spot 150. Once the signals have passed through the spatial separation component of the optical train, e.g., prism 108, and are focused onto the detector, they are spatially separated into their respective different optical signal components, as represented by spots 152 and 154.

Figure 2:
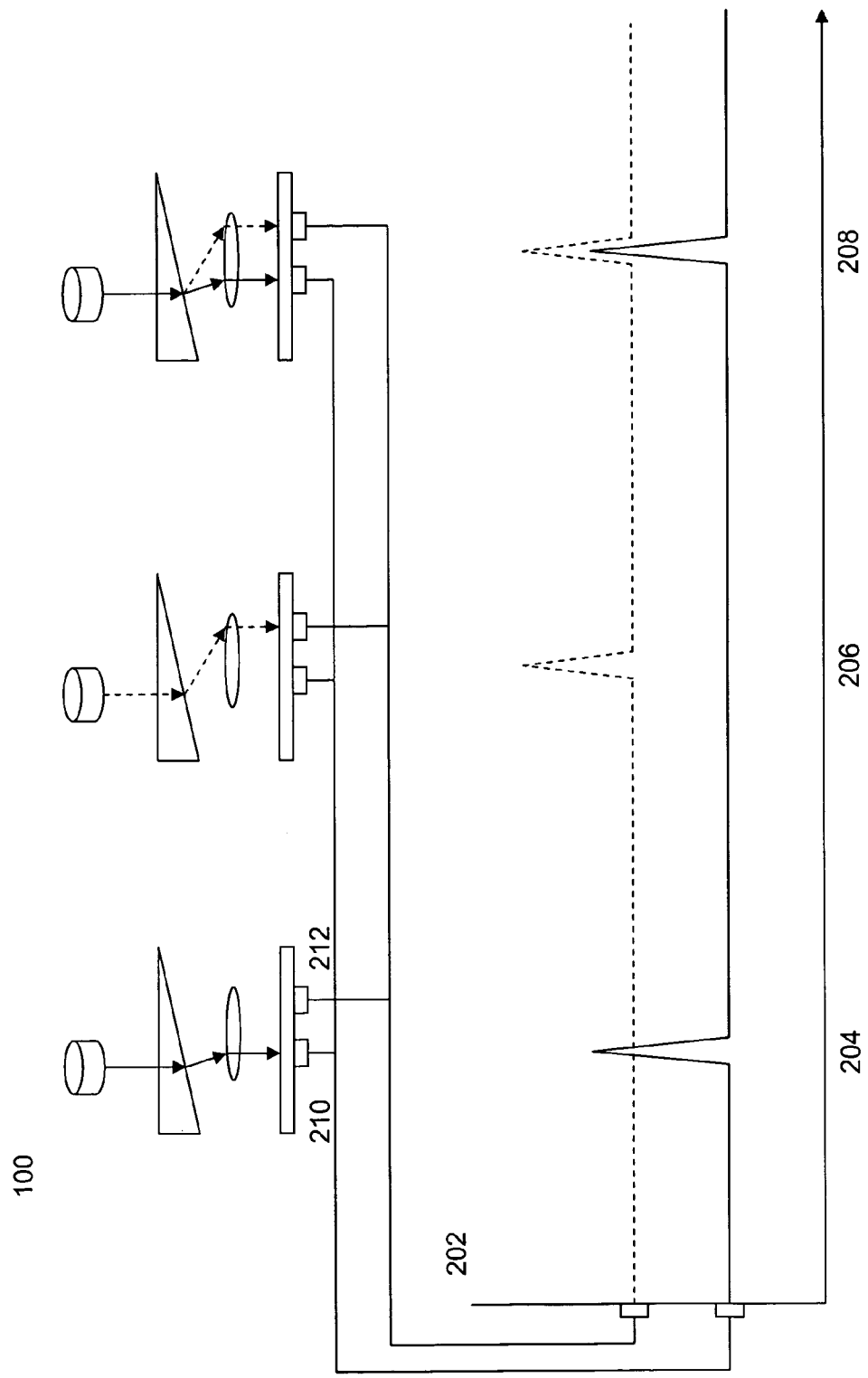
FIG. 2 provides a schematic illustration of the operation of the systems and methods of the invention in monitoring multiple different optical signals over time.

FIG. 2 schematically illustrates the detection operations over a period of time, where the signals are concurrent or not. In particular, as shown, the system 100 is further connected to a recording/readout system, schematically illustrated as plot 202. Over time, as indicated by the horizontal axis of plot 202, different optical signals emanate from the confined source 106, either at different times (as shown at times 204 and 206) or concurrently (at time 208). The optical signals are detected on different locations of the detector 112, where each location is separately connected to the recording system (e.g., and connections 210 and 212). As a result, optical signals from a single confined source are separately detected and recorded, and can be attributed to a given point in time.

One exemplary use of the methods of the present invention is in the performance of nucleic acid sequence analysis processes, and particularly single molecule based processes that analyze nucleic acid sequences by monitoring the template dependent synthesis of complementary nucleic acid sequences through the detection of differently labeled nucleotide analogs that are incorporated into the growing synthesized strand. See, e.g., U.S. patent application Ser. Nos. 2003/0044781 A1, which is incorporated herein by reference in its entirety for all purposes.

In one such method, a DNA polymerase enzyme is associated or complexed with a template nucleic acid sequence, which is immobilized on the surface of a substrate, attached through either the template or the polymerase. The complex is exposed to appropriate polymerization reaction conditions, including differently labeled nucleoside polyphosphates, e.g., nucleoside triphosphates (NTPs), nucleoside tetraphosphates, nucleoside pentaphosphates, etc., or analogs of any of these, or other nucleoside or nucleotide molecules, that are incorporated by polymerase enzymes (all of which are referred to herein as NTPs, for convenience), where each different NTP (e.g., A, T, G, or C) is labeled with fluorescent label having a different emission wavelength profile. Incorporation of each different type of NTP produces a different optical signal indicative of the incorporation event. For example, in methods employing a confined volume containing the immobilized polymerase/template complex, the incorporation of a given fluorescent base results in that base being held within the detection region for longer periods than bases that are not incorporated. By detecting the signal associated with an incorporated base, one can identify, in sequence, the bases that are incorporated in the template dependent synthesis. In accordance with the invention, each incorporation signal, generally characterized as a fluorescent pulse, is directed to a different location on an optical detector array, and identified based upon that location upon the detector array. Thus, as shown in FIG. 2, different optical signals are generated within a single confined source, although they may be generated at different times, e.g., sequentially as each base is incorporated.

In such cases, the polymerization reaction environment is confined by virtue of its immobilization on the surface of the substrate, but is also typically further, structurally confined, e.g., in a zero mode waveguide and/or within a reaction well in a multiwell plate.

In another example, a nucleic acid strand, e.g., a polynucleotide, is immobilized upon the surface of a substrate and interrogated with nucleic acid probes having different optical labels associated with them. By identifying the probes that hybridize, e.g., remain localized, within the confined area of the immobilized nucleic acid, one can identify the sequence of the immobilized sequence. Likewise, where the immobilized sequence is known, one can identify the sequence of the probe sequences that hybridize to it.

Figure 4:
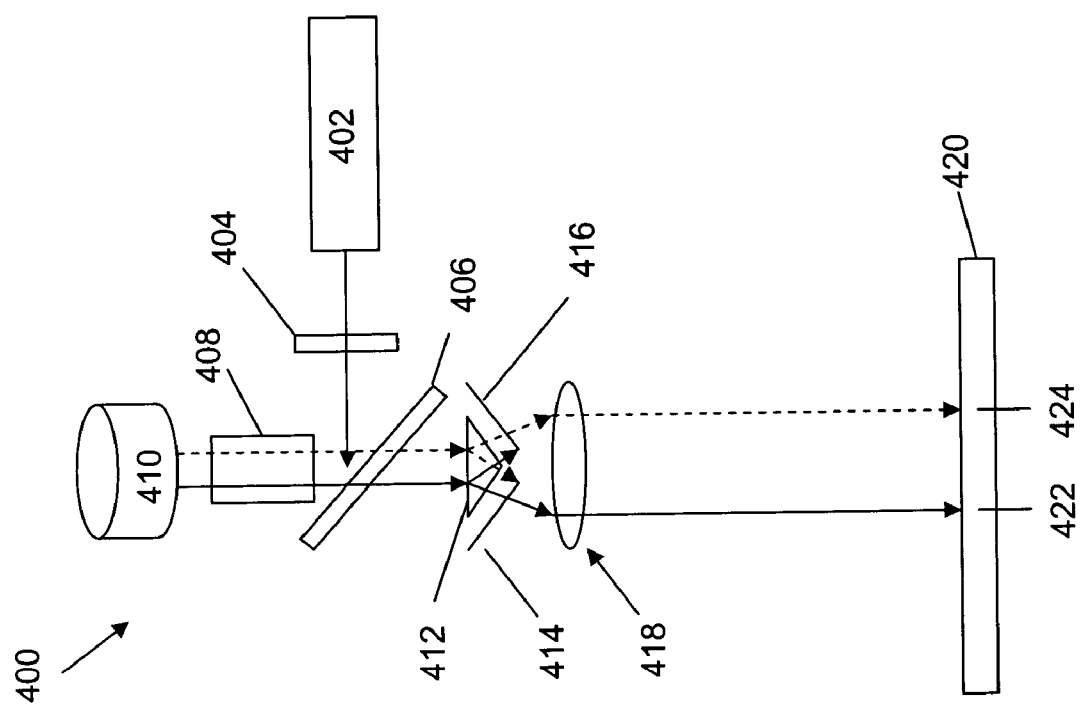
FIG. 4 schematically illustrates an alternate system configuration for monitoring multiple optical signals that differ in their relative polarization, as opposed to other characteristics of light, e.g., wavelength.

In a further example, assays that detect differences in fluorescent polarization capabilities of substrate and product may be monitored using the methods and systems of the invention. By way of example, U.S. Pat. No. 6,699,655, which is incorporated herein by reference in its entirety for all purposes, describes homogeneous assay systems that are capable of monitoring reactions in which reactants and products have substantially different charges. Such assays include kinase or phosphatase assays where phosphorylated or dephosphorylated products have substantially different charges as compared to their substrates, as a result of addition or removal of a phosphate group, nucleic acid hybridization assays, protease assays, and the like. Briefly, a large, charged molecule or other structure associates differentially with a substrate or product, based upon the charge differential, and thus changes the rotational diffusion of the substrate or product, consequently changing the relative polarization of fluorescence emitted from an attached fluorescent label in response to polarized excitation radiation. In conjunction with the present invention, rather than directing the different planar components of depolarized fluorescence to separate detectors, the two different signals are first spatially separated, and then directed to different locations on the same detector. An example of a system for use in performing applications that distinguish among different polarized optical signals is shown in FIG. 4.

It will be appreciated that although described with respect to certain types of assays, the methods of the invention are useful in a variety of different analytical contexts where two or more optical signals emanate from a single confined source, but one desires to detect, record and/or monitor them separately, including the use of internal control signals, and the like.

III. Systems

Figure 3:
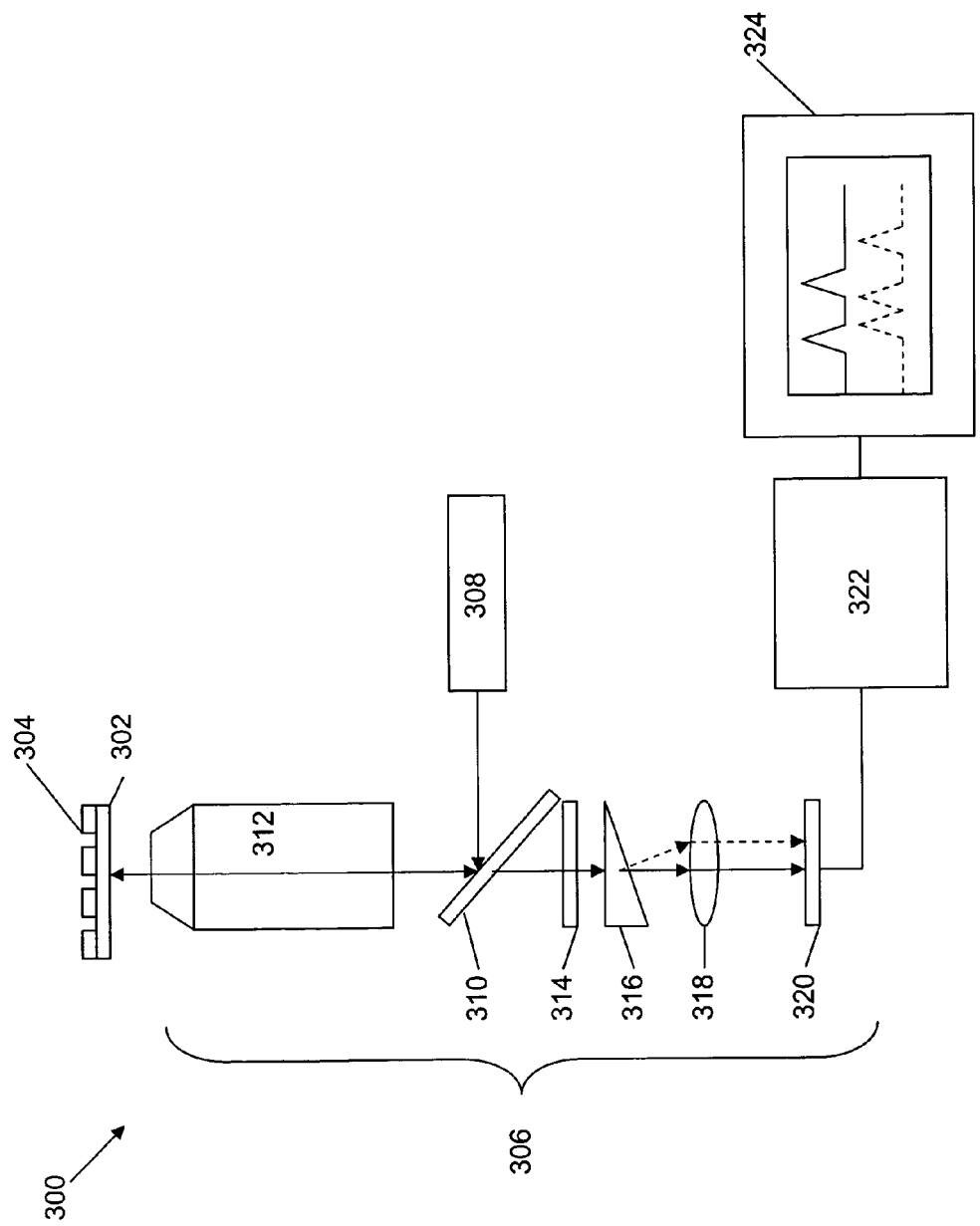
FIG. 3 schematically illustrates one exemplary system according to the present invention in greater detail.

The present invention also provides for systems and devices useful in carrying out the above-described methods. FIG. 3 schematically illustrates one exemplary system for carrying out the methods of the present invention. As shown, the overall system 300 includes a source of at least two different optical signals 302. As shown, source 302 comprises a substrate that includes at least one, and preferably an array of zero mode waveguides 304 fabricated thereon. An optical train 306 is also provided that is in optical communication with the source 302, including waveguides 304. As shown, optical train 306 includes a source of excitation radiation, e.g., a laser 308, laser diode, LED, or the like, for use with fluorescent or fluorogenic optical signaling components within the source 302. Also included in the optical train shown 306, is a dichroic mirror 310 that reflects excitation radiation to direct it toward the source 302, e.g., including waveguide 304, but that will pass emitted fluorescence. An objective lens or other focusing lens 312 is also typically provided to focus and further direct excitation radiation to and optical signals, e.g., fluorescence, from source 302. In the system illustrated, the signal is passed through a barrier or notch filter 314 to further reduce any excitation radiation not reflected by dichroic 310, and then through a prism 316 or optical grating is provided to spatially separate excitation radiation by, e.g., wavelength, and direct it through lens 312, and onto an optical detector, e.g., CCD 320. Useful prisms and/or optical gratings are generally commercially available from a variety of commercial optics suppliers, including, e.g., Thorlabs, Inc. (New Jersey), Newport Corp (Irvine, Calif.), CVI Corporation (Alberquerque, N. Mex.), and the like. The signals detected upon CCD 320, including their intensity and location/pixel identification, are recorded by processor 322 which may perform one or more data manipulations on such recorded signal data (e.g., to assign a reaction parameter, etc.) and then provided in a user friendly readout format, e.g., on display 324.

Although shown as a single prism or grating, it will be appreciated that in some cases, it may be desirable to use more than one prism. In particular, in some cases, the spatial separation of different signals resulting from the dispersion profile of a given prism may not achieve a desired spatial separation. For example, in cases of high density of detector elements in a detector array, it may be desirable to provide for regularly or linearly spaced signal components. However, the dispersion profiles of given prism may not be linear, e.g., the resulting transmitted signals are not equally spatially separated. However, where detection is facilitated by ensuring all signals have similar separation relative to each other, e.g., in using CCDs for detecting dense collections of signals, it may be advantageous to combine prisms with dissimilar dispersion profiles to provide a near linear separation profile for each of the signals being detected. Likewise, in certain cases, detection of different signals may be optimized by providing greater separation between two or more signal components than a linear separation might afford. In such cases, the tunability of two or more prisms allows for this increased flexibility of the system. In addition to the use of additional prisms or gratings, it will be appreciated that tuning of the system may be accomplished by rotating the prism or other dispersive optical element, e.g., around the optical axis of the optical system and also perpendicular to the direction of color separation, to adjust the degree of dispersion. Thus, in system embodiments, it may be useful to provide one or more of the prisms in a configuration that is capable of being readily rotated about the axis.

In operation of the system shown, the source of different optical signals 302 includes a reaction mixture that generates products, or consumes substrates that produce at least two different optical signals, e.g., substrates, intermediates and/or products that bear fluorescent labels that emit light at differing wavelengths. Light source, e.g., laser 308, directs excitation radiation, e.g., light at an appropriate excitation wavelength for the fluorescent labels present in the source 302, toward dichroic 310. The excitation radiation is reflected by dichroic 310, through objective 312, to impinge upon the source 302, thus exciting the fluorescent labels contained therein. The emitted fluorescence is again collected by objective 312 and directed through dichroic 310, which is selected to reflect light of the wavelength of the excitation radiation, but pass light of the wavelength(s) of the emitted fluorescence. As a result, any reflected excitation radiation is filtered away from the fluorescence. The fluorescent signal(s) are then directed through a prism 316 or optical grating that spatially separates the differing signals by wavelength, and then refocused using a lens 318, e.g., an imaging lens, and directs them to different locations on an optical detector array, e.g., CCD 320, photon counting avalanche photodiode array, photomultiplier tube (PMT) array or the like. A variety of different detector arrays may be employed in the invention, including, e.g., diode arrays, CCD arrays, and the like. CCDs are generally preferred for their compact nature, high resolution and cost, and may generally be employed as the detector. Various types of CCDs may be employed to suit the needs of a given analysis, including, for example, standard CCDs, electron multiplier CCDs (EMCCD), and/or Intensified CCD (ICCD).

As noted above, a modified system of the invention may be employed to monitor signals that differ in other optical characteristics. In particular, FIG. 4 is a schematic illustration of a system that directs optical signals that differ from each other in the relative polarity of the emitted fluorescence. Such detection may be employed in monitoring reactions that yield substantial size changes on products or reactants, and consequently changes in the reactant or product's ability to emit depolarized fluorescence (See, e.g., U.S. Pat. No. 6,699,655). By measuring light emitted in two orthogonal planes, one can assess the relative depolarization of fluorescent emissions in response to polarized excitation light. As shown, the system, 400, again includes an activation light source 402 that is directed through a dichroic filter 406 and objective 408 toward a confined reaction vessel or region 410. Light source 402 may comprise a polarized light source or be directed through a polarizing filter 404 to provide polarized excitation radiation to the reaction vessel 410. Emitted fluorescence is then collected by objective lens 408 and directed through beam splitter 412, where it is split into two similar beams. Each beam is then separately passed through one of two oppositely polarized filters 414 and 416, such that only fluorescence in one of the two orthogonal planes is passed through lens 418 to each of the regions 422 and 424 on detector array 420. The location of each signal on the detector array is an indication of which plane of fluorescence is being detected. The intensity of the signals are then compared to determine the relative depolarization of fluorescence from the reaction mixture (See, again, U.S. Pat. No. 6,699,655).

IV. Examples

Figure 5B:
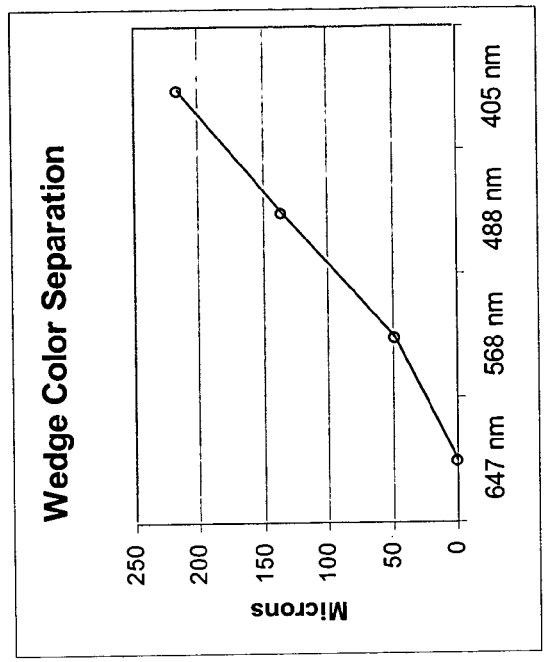
FIG. 5B shows the relative distance of separation between separated signals.
Figure 5A:
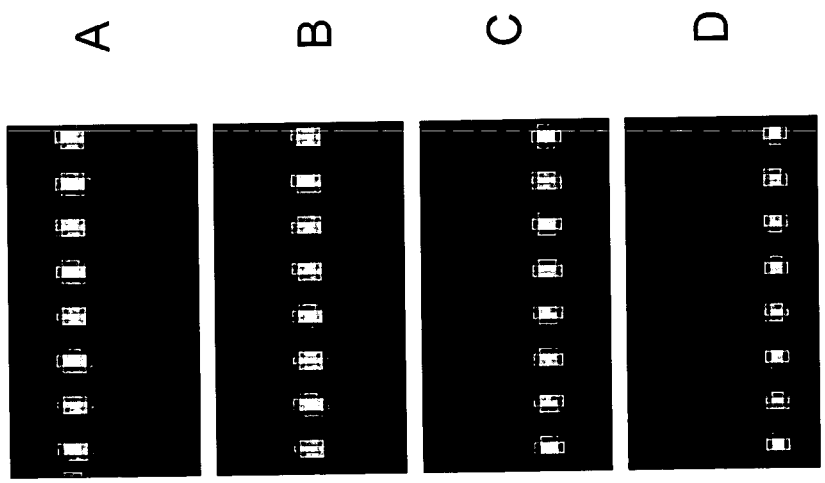
FIG. 5A shows different optical signals incident upon different locations of a single CCD camera chip, which were derived from a single, combined source, and subjected to the methods of the invention.

To test the efficacy of the optical train in separating multiple optical signals from a confined source, a system was set up that was substantially similar to the system shown in FIG. 3. As shown, the system included a substrate having a series of zero-mode waveguides fabricated thereon. The substrate was positioned proximal to and within optical communication of objective lens, and a white light source was positioned above the zero mode waveguide substrate and directed through a narrow band filter, at the waveguide substrate. An objective lens was used to focus optical signals from the waveguides through wedge prism. Once separated by wedge prism, the different optical signals were then passed through the imaging lens onto a 512×512 pixel EMCCD camera chip. In operation, the broadband light (made up of a subset continuum of the white light spectrum), collected by the objective lens and then passed through a wedge prism was then focused, as a collection of separated signals, upon the CCD camera. FIG. 5A illustrates the images derived from four different regions of the CCD, corresponding to light from the eight different zero mode waveguides and four different wavelengths, 405 nm (A), 488 nm (B), 568 nm (C) and 647 nm (D). FIG. 5B is a plot of the relative location, in distance from a position of an unseparated signal, in microns, showing the relative separation distance between the separated signals.

A comparison experiment was also performed to demonstrate the increased efficiency of the prism based separation as compared to a filter based wavelength separation. In particular a mixture of two different fluorescent dyes (Alexa488 and Alexa568, available from Molecular Probes, Eugene, Oreg.) having different peak emission wavelengths (488 nm and 568 nm, respectively) was prepared and interrogated using appropriate excitation radiation. Emissions from the mixture were passed through an objective and subjected to either filter based wavelength separation (using two Semrock triple notch filters, or wedge prism based separation, prior to focusing the separated signals onto a CCD chip. The table, below, provides fluorescence intensities of each signal in each different optical train, as measured using an EMCCD. As can be seen, the prism based separation yields substantially higher efficiency detection of the separated signal as compared to the filter based system.

| Separation Method | Fluorescent Intensity Detected | |
| --- | --- | --- |
| | Alexa488 | Alexa568 |
| Filter based separation | 1146 | 1263 |
| Prism Separation | 2845 | 2676 |

Although described in some detail for purposes of illustration, it will be readily appreciated that a number of variations known or appreciated by those of skill in the art may be practiced within the scope of present invention. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes.

What is claimed is:

1. A method of detecting optical signals, comprising:
   simultaneously illuminating over time each of a plurality of fluid confinements on a substrate with an excitation radiation to produce at least first and second optical signals from each fluid confinement; the at least first and second optical signals produced during the occurrence of different reactions of chemical species, wherein at least one of the chemical species is immobilized on the substrate within each fluid confinement and a chemical species with which it reacts is fluid borne, and the first and second optical signals occurring at different times within each fluid confinement wherein the first optical signal comprises a wavelength different from a wavelength of the at least second optical signal;
   passing the at least first and second optical signals through an optical train that transmits the first and second optical signals in divergent paths;
   receiving the first and second optical signals at different locations on one optical detector.

2. The method of claim 1, wherein the fluid confinement comprises at least a third optical signal, which comprises a wavelength different from a wavelength of the at least first and second optical signals.

3. The method of claim 2, wherein the third optical signal is spatially separated from the first and second optical signals and directed to a third location on the one optical detector different from the first and second locations.

4. The method of claim 3, wherein the fluid confinement comprises at least a fourth optical signal, which comprises a wavelength different from a wavelength of the at least first, second and third optical signals.

5. The method of claim 4, wherein fourth optical signal is spatially separated from the first, second and third optical signals and directed to a fourth location on the one optical detector different from the first, second and third locations.

6. The method of claim 2, wherein the third optical signal is spatially separated from the first and second optical signals and directed to a first location on a second optical detector.

7. The method of claim 2, wherein the at least first and second optical signals are at least partially concurrent.

8. The method of claim 2, wherein the source comprises at least first and second fluorescent components that emit the first and second optical signals, respectively.

9. The method of claim 8, wherein the first and second fluorescent components comprise first and second fluorescent labels covalently coupled to at least first and second different nucleotide polyphosphates or nucleotide polyphosphate analogs.

10. The method of claim 9, wherein the fluid confinement comprises a zero mode waveguide.

11. The method of claim 10, wherein at least one of the chemical species comprises a complex of polymerase, template nucleic acid and primer sequence complementary to a portion of the template nucleic acid, immobilized within the zero mode waveguide, and wherein first and second optical signals are produced when first and second different nucleotide polyphosphates or nucleotide polyphosphate analogs bearing the first and second fluorescent labels, respectively, are associated with the complex.

12. The method of claim 2, wherein spatially separating the first and second optical signals comprises passing the first and second optical signals through an optical train that directs the first and second optical signals on divergent paths.

13. The method of claim 12, wherein the optical train comprises an optical grating for spatially separating the first and second optical signals.

14. The method of claim 12, wherein the optical train comprises a prism for spatially separating the first and second optical signals.

15. The method of claim 2, further comprising characterizing the first and second optical signals based upon the location on the detector to which they were directed.

16. The method of claim 2, wherein the source comprises an unknown optical signal, the method further comprising characterizing whether the unknown optical signal is the first or second optical signal by a location upon the one detector to which the unknown optical signal is directed.

17. The method of claim 1 wherein the reactions of chemical species comprises DNA sequence identification, DNA hybridization, immunoassays, or enzymatic reactions.

18. An analytical system, comprising:
a plurality of confined reaction regions on a substrate for containing a reaction mixture that each produce at least first and second optical signals by illumination with excitation light of different reactions of chemical species within each confined reaction region, wherein at least one of the chemical species is immobilized on the substrate within the confined reaction region and the a chemical species with which it reacts is fluid borne, such optical signals produced during the reactions, and occurring at different times, wherein the first optical signal comprises a wavelength different from a wavelength of the at least second optical signal;
an excitation light source; and
an optical train in optical communication with the confined reaction regions, for simultaneously directing excitation light from the light source to the plurality of confined reaction regions over time, and receiving the first and second optical signals from the plurality of confined reaction regions and spatially separating the first and second optical signals and directing them to different locations on an optical detector.

19. The analytical system of claim 18, wherein the optical detector comprises a photodiode array.

20. The analytical system of claim 18, wherein the optical detector comprises a charge coupled device (CCD).

21. The analytical system of claim 18, wherein the optical train comprises an optical grating that spatially separates the first and second optical signals directed therethrough.

22. The analytical system of claim 21, wherein the optical train comprises an optical grating that spatially separates the first, second and third optical signals directed therethrough.

23. The analytical system of claim 22, wherein the optical train comprises an optical grating that spatially separates the first, second, third and fourth optical signals directed therethrough.

24. The analytical system of claim 18, wherein the optical train comprises a first prism that spatially separates the at least first and second optical signals.

25. The analytical system of claim 24, wherein the optical train further comprises at least a second prism in series with the first prism.

26. The analytical system of claim 25, wherein at least one of the first and second prisms is rotatable around an optical axis of the optical train to adjust a dispersion profile of the optical signals passing therethrough.

27. The analytical system of claim 18, wherein the confined reaction region comprise wells in a multiwell plate.

28. The analytical system of claim 18, wherein confined reaction region comprises a feature on a molecular array.

29. The analytical system of claim 18, wherein the confined reaction regions comprise zero mode waveguides.

30. The analytical system of claim 18, further comprising a processor operably coupled to the detector for individually or collectively recording the first and second optical signals incident upon the different locations on the detector and characterizing the first and second optical signals based upon the different location on the detector upon which said optical signals were incident.

31. An analytical system, comprising:
a plurality of confined reaction regions on a substrate for containing a reaction mixture that produces in each confined region at least first and second optical signals resulting from the illumination of different reactions of chemical species occurring in each confined region, wherein at least one of the chemical species is immobilized on the substrate within the confined reaction region and a chemical species with which it reacts is fluid borne, such optical signals produced during the reactions, and occurring at different times, wherein the first optical signal comprises a wavelength different from a wavelength of the at least second optical signal;

an optical train in optical communication with the confined reaction region, for simultaneously illuminating over time each of the plurality of confined reaction regions, and for receiving the first and second optical signals from the plurality of confined reaction regions and spatially separating the first and second optical signals and directing them to different locations on an optical detector, wherein said optical train comprises a replaceable modular optical component that spatially separates the first and second optical signals passing therethrough.

32. The analytical system of claim 31, wherein the replaceable modular component comprises at least a first prism.

33. The analytical system of claim 32, wherein at least one of the first and second prisms are rotatable around an optical axis of the optical train.

34. The analytical system of claim 31, wherein the modular component comprises at least the first prism and a second prism.

35. The analytical system of claim 31, wherein the replaceable modular component comprises an optical grating.

36. The analytical system of claim 31, further comprising a library of a plurality of replaceable modular components, wherein each of the plurality of modular components has a different dispersion profile for different optical signals.

37. A method of detecting optical signals, comprising:
simultaneously illuminating a plurality of fluid confinements on a substrate over time to produce first and second optical signals from each fluid confinement;
the first and second optical signals produced during different reactions of chemical species in each fluid confinement, and occurring at different times within each fluid confinement, wherein at least one of the chemical species is immobilized on the substrate within the fluid confinement and a chemical species with which it reacts is fluid borne, and wherein the first optical signal comprises an optical characteristic different from an optical characteristic of the at least second optical signal;
passing optical signals through an optical train that transmits the first and second optical signals in divergent paths; and
receiving the first and second optical signals from each of the plurality of fluid confinement at different locations on one optical detector.

38. A method of detecting optical signals, comprising:
simultaneously illuminating a plurality of fluid confinements on a substrate over time to produce first and second optical signals from each fluid confinement;
the at least first and second optical signals produced during different reactions of chemical species in each fluid confinement, wherein at least one of the chemical species is immobilized to the substrate within the fluid confinement and a chemical species with which it reacts is fluid borne, and the at least first and second optical signals occurring at different times within the fluid confinements, wherein the first optical signal comprises a wavelength different from a wavelength of the at least second optical signal; and
directing the first and second optical signals from each of the plurality of fluid confinements to different locations on one optical detector.

39. A method of detecting optical signals, comprising:
simultaneously illuminating a plurality of fluid confinements on a substrate over time to produce first and second optical signals from each fluid confinements;
wherein each different optical signal is produced from the illumination of a different reaction of chemical species in each fluid confinements, wherein at least one of the chemical species is immobilized on the substrate within each fluid confinement and a chemical species with which it reacts is fluid borne, such optical signals produced during the reactions, and occurring at a different time and comprises a wavelength different from each other optical signal; and
spatially separating the plurality of different optical signals from each of the plurality of fluid confinements and directing them to discrete locations on one optical detector.

40. A method of detecting optical signals, comprising:
illuminating a fluid confinements on a substrate continuously over time to produce at least first and second optical signals;
the at least first and second optical signals produced from the illumination of different reactions of chemical species, wherein at least one of the chemical species is immobilized on the substrate within each fluid confinement and a chemical species with which it reacts is fluid borne, such optical signals produced during the reactions, and occurring at different times, and wherein the first optical signal comprises a wavelength different from a wavelength of the at least second optical signal; and
spatially separating the first and second optical signals and directing the first and second optical signals to first and second different locations on a first optical detector.

* * * * *